United States Patent [19]

Behan et al.

[11] Patent Number: 5,374,614

[45] Date of Patent: Dec. 20, 1994

[54] AQUEOUS PERFUME OIL MICROEMULSIONS

[76] Inventors: John M. Behan, Shermel, Ball Lane, Kennington, Ashford, Kent; Jeremy N. Ness, 22 River Court, Chartham, Canterbury, Kent, both of Great Britain; Petrus C. Traas, Amersfoortsestraatweg 132, 1411 HK Naarden; Joannis S. Vitsas, Bisonstraat 15, 1402 TX Bussum, both of Netherlands; Brian J. Willis, Fleets Lane, Tyler Hill, Canterbury, Kent, Great Britain

[21] Appl. No.: 68,680

[22] Filed: May 28, 1993

[30] Foreign Application Priority Data

May 29, 1992 [EP] European Pat. Off. ............ 92304923

[51] Int. Cl.$^5$ ................................................ A61K 7/46
[52] U.S. Cl. ............................................ 512/3; 512/4
[58] Field of Search .................................. 512/2, 4, 3

[56] References Cited

U.S. PATENT DOCUMENTS

| | | | |
|---|---|---|---|
| 4,170,655 | 10/1979 | Zeidler et al. | 512/3 |
| 4,299,737 | 11/1981 | Meffert et al. | 512/2 |
| 5,079,227 | 1/1992 | Handjani et al. | 512/2 |
| 5,246,918 | 9/1993 | Behan et al. | 512/2 |
| 5,252,555 | 10/1993 | Dartnell | 512/2 |
| 5,283,056 | 2/1994 | Chung et al. | 512/3 |

FOREIGN PATENT DOCUMENTS

| | | | |
|---|---|---|---|
| 261351 | 3/1988 | European Pat. Off. | 512/3 |
| 316726 | 5/1989 | European Pat. Off. | 512/3 |
| 516508 | 12/1992 | European Pat. Off. | 512/3 |
| 2372226 | 6/1978 | France | 512/3 |
| 2639293 | 3/1978 | Germany | 512/2 |
| 2731218 | 2/1979 | Germany | 512/2 |

OTHER PUBLICATIONS

T. Joseph Lin, Microemulsions and Application of Solubilization in Cosmetics, Surfactants Science Series, vol. 16, 1985, pp. 29–53.

*Primary Examiner*—James H. Reamer
*Attorney, Agent, or Firm*—Cushman, Darby & Cushman

[57] ABSTRACT

The invention concerns clear o/w microemulsions comprising a perfume oil, an aqueous phase and one or more surfactants with HLB between 9 and 18, and co-surfactants of which at least 0.5% of ionic co-surfactant. The weight ratio of perfume oil to total surfactant is between 0.85 and 2.5, and preferably above 1. The quantity of perfume oil is 0.01–40% w/w, preferably below 35%, of the microemulsion and the quantity of water at least 40% w/w, preferably at least 50%. The microemulsions comprise less than 10% preferably less than 5%, of alcohol. The surfactants are preferably of the nonionic type.

The microemulsions are very suitable for perfuming purposes where the amount of organic solvents should preferably be kept to a minimum, such as for perfuming skin or hair.

The invention also concerns surfactant/perfume mixtures suitable for preparing the clear o/w microemulsions.

16 Claims, No Drawings

AQUEOUS PERFUME OIL MICROEMULSIONS

This invention concerns clear aqueous perfume oil microemulsions. More particularly the invention concerns perfume oil microemulsions of the o/w type wherein limited amounts of surfactants are used for solubilizing the perfume oil. Also, this invention concerns a method for applying perfume to the skin using these clear aqueous perfume oil microemulsions. Finally, this invention concerns surfactant/perfume oil mixtures suitable for preparing the clear aqueous perfume oil microemulsions.

Traditionally, perfumes are provided dissolved in a suitable solvent. Such solvents may be lower aliphatic alcohols such as ethanol or isopropanol, glycol ethers and other organic solvents and mixtures of such solvents with water. Perfumes intended for application to the skin are often dissolved in ethanol or in ethanol/water mixtures with a high ethanol content.

Ethanol and other lower aliphatic alcohols have several disadvantages as perfume solvents. They are volatile and flammable and thus present a fire hazard in production and use. They are relatively expensive. They are not completely innocuous to health. Ethanol, which is the most acceptable of them from a health point of view, is heavily taxed in many countries and not allowed for religious reasons in some islamic countries. They have a distinct odour, which may interfere with the perfume.

Thus, it would be advantageous to substantially eliminate these alcohols as perfume solvents and instead thereof admix perfume with water, which is cheap, innocuous, non-flammable and odourless. However, most perfumes are substantially immiscible with water, and therefore such mixtures would be emulsions. To be suitable for many applications where traditionally alcoholic solutions have been used, such emulsions should be physically stable and substantially clear and thus should be of the microemulsion-type.

Perfume microemulsions in water with no or only minor amounts of alcohols or other organic solvents are known in the art. However, the inherent hydrophobicity of most perfumes requires the presence of substantial amounts of surfactants as solubilizing agents. Surfactants which have been found suitable in the art for solubilizing perfumes in water have been anionics or mixtures thereof with smaller amounts of non-ionics. Thus, J. M. Blakeway et al, Int. J. Cosmet. Sc. 1, (1979), 1–15, described microemulsions of up to 4% w/w perfume in water wherein at least 3 times the amount of sodium laurylether sulphate, monoethanolamine lauryl sulphate or combinations thereof with a minor amount of coconut diethanolamide were needed to obtain a clear microemulsion. T. J. Lin, Surfactants in Cosmetics, Surfactants Sci. Ser. Vol. 16, (1985), 29–52, mentions the necessity of having a surfactant to oil ratio of much greater than unity to prepare practical o/w microemulsions. GB-A-2190681, EP-A-0316726 and EP-A-0368146 all describe clear aqueous perfume microemulsions for hard surface cleaning purposes. Although very wide theoretical limits for perfume, anionic surfactant and non-ionic surfactant content are given in the specification, it is clear from the examples that the surfactants are always used in substantial excess to the amount of perfume. Most examples specify a surfactant/perfume ratio 7:1; one example specifies 7:3. The anionic/non-ionic surfactant ratio is a 4:3 in all examples. Also, organic solvents such as low molecular weight alcohols are preferably added as so called co-surfactants. In U.S. Pat. No. 4,170,655 clear stable aqueous solutions of fat-soluble perfumes are described wherein specific hydroxyalkylester- and/or N-(hydroxyalkyl)amide-ethoxylates are used in concentrations of 0.1–20% w/w, preferably 0.5–5%, to solubilize 0.1–1% w/w of the perfume in the aqueous solution. In U.S. Pat. No. 4,299,737 hydroxyalkylether-propoxyethoxylates are described for the same purpose in the same relative amounts. In both patent specifications 7:3 and 8:2 surfactant/perfume ratios were used in all examples. In EP-A-0278660 clear homogeneous microemulsions are described containing at least 20% w/w of hydrophobic phase, at most 20% of hydrophilic phase, up to 20% of cationic quaternary ammonium surfactant and a wide range of compounds as possible co-surfactants. The hydrophilic phase may comprise appreciable quantities of alcohol.

Perfumes may also be solubilized using non-ionic surfactants. Most of the prior art in this area specifies the use of non-ionic surfactants in a quantity which is much higher than the quantity of perfume, typically 2–4 times the amount of perfume. M. Tagawa et al, J. Soc. Cosmet. Chem. Japan, 13 (1), (1979), 47–51, studied the solubilization of limonene with various ethoxylated/-propoxylated 2-decyl-tetradecylethers and with ethoxylated hydrogenated castor oil with various oxyethylene chain lengths and in the presence of various quantities of ethanol and found that for the first group of surfactants a perfume/surfactant ratio of below and for the second group even below 0.4 was needed in order to obtain clear microemulsions. S. J. Strianse and M. Lanzet, The Toilet Goods Association, Proc. Sc. Sec. No. 34, December 1960, 8–18, describe the solubilization of 1% and 3% lavender oil, lime oil and methyl salicylate in water, using mixtures of: ethoxylated nonylphenol ammonium sulphate with ethoxylated isooctylphenol, ethoxylated isooctylphenol with ethoxylated sorbitan monolaurate and a blend of different ethoxylated lauryl ethers respectively. Only with the first mentioned surfactant mixture they were able to obtain clear lavender and lime oil microemulsions using a perfume/surfactant ratio of 0.83 for 1% oil and a ratio of 1 for 3% oil. The other surfactant mixtures needed perfume/surfactant ratios of 0.66 to as much as 0.1 for clear microemulsions.

Various theoretical considerations on the preparation and use of o/w microemulsions have been given by Lin, Surfactants in Cosmetics (vide supra) and literature cited therein, in "The HLB System", published by ICI Americas Inc, Wilmington, Del., and in Aveyard et al, J. Chem. Tech. Biotechnol. 48 (1990), 161–171.

For many applications the aqueous perfume microemulsions described in the art are not completely satisfactory for substituting perfume solutions in organic solvents, particularly ethanol or aqueous ethanol. The presence of large quantities of surfactants is often undesirable for various reasons: they add to the cost of the total formulation without having any beneficial effect after use of the microemulsion; they may leave a sticky film on a surface to which the perfume is applied, which is particularly a disadvantage if that surface is the skin; they may have a disagreeable odour; they tend to diminish the perceived odour strength of the perfume. Furthermore, especially in perfume formulations which are applied to and intended to be left on skin or hair, the presence of certain surfactants, notably anionic surfactants, should be limited because of possible adverse reactions with the skin, see T. J. Lin, supra. Stable aueous and aqueous-alcoholic perfume solutions have been described in EP-A-0261351 which require a C1-6 alkanol propylene oxide and ethylene oxide polymer and a non-ionic emulsifier. However, this reference does not require the solutions to be clear and it has been found that often up to 20% alcohol is still needed to obtain clear microemulsion. Thus, the stability and/or clarity of these solutions often leaves something to be desired, This may not always be a problem if the solutions are intended for incorporation into other cosmetic formulations or room deodorants, as described in this reference, but it is undesirable when they are intended for use as such by the consumer.

However, it has now been found that stable clear o/w microemulsions of perfume oil in water may be obtained using only limited quantities of certain surfactant mixtures. It has also been found that such microemulsions are excellently suitable for use in those applications where traditionally alcoholic perfume solutions have been used, notably for application to skin or hair. Furthermore, it has been found that the microemulsions according to the invention are very suitable for clear air fresheners, e.g in the form of clear gels. Thus, the microemulsions according to the invention comprise perfume oil, aqueous phase, a primary surfactant and one or more co-surfactants including a quantity of an ionic co-surfactant. Preferably the primary surfactants are predominantly or even exclusively non-ionic if the microemulsions are intended for skin or hair application. Finally surfactant/perfume oil mixtures have been found comprising perfume oil, a primary surfactant and one or more co-surfactants including a quantity of an ionic co-surfactant.

For the purpose of this invention "clear" as applied to the microemulsions is intended to mean transparent or translucent when observed through a layer of not more than 10 cm thickness. Also, the term "microemulsion is intended to mean an emulsion having a mean droplet size of the oil phase of 100 nm or less.

The quantity of perfume oil in the microemulsion is largely determined by the intended use of the microemulsion. Thus, an important consideration is whether the consumer will use the microemulsion as such, or whether the microemulsion is intended for addition to another consumer product to incorporate a perfume therein, and will thus be diluted through addition to that product. Another important consideration is whether the perfumed product usually will be relatively highly perfumed, i.e. has an actual perfume content of 1% w/w or more, or relatively weakly perfumed, i.e. below 1% perfume content. Highly perfumed products are e.g.: products intended for perfuming the skin, wick-type air fresheners and certain hard surface cleaners. Weakly perfumed products are e.g.: water-based air fresheners, toilet cleaners, bleaches, cold wave lotions, window cleaners. Thus, the minimum quantity of perfume oil should be such as to be useful for the purpose for which the microemulsion is used.

In general a minimum perfume oil content of at least 0.01% w/w will be required for all purposes. For highly perfumed microemulsions the perfume oil content is also more than 1% w/w of the microemulsion, particularly more than 3%. For weakly perfumed microemulsions still the perfume oil content should preferably be 0.05% w/w or more. For microemulsions intended for addition to other consumer products the content of perfume oil will be determined by the perfume oil requirement of the final consumer product and the degree of dilution brought about by adding the microemulsion to the other components of the consumer product.

The maximum quantity of perfume oil is determined by the maximum quantity that can be accomodated in a clear o/w microemulsion, which in turn is dependent on the hydrophobicity of the perfume oil. In general however the maximum quantity will be not more than 40% w/w of the microemulsion. Preferably the quantity of perfume oil should be kept at 35% or below. The minimum quantity of water necessary to obtain a clear o/w emulsion will generally be at least 40% w/w of the microemulsion. Preferably the quantity of the aqueous phase is at least 50%, more preferably at least 60%, particularly at least 70%. For low perfume content products the quantity of aqueous phase will generally be at least 80% w/w.

The perfume oil may be a perfume per se as hereinafter more fully defined, or it may be a homogeneous mixture of a perfume with one or more other lipophilic liquids. Such liquids may be added for solvent purposes only, e.g. to reduce the viscosity of the perfume, to aid in dissolving certain solid perfume components, or to reduce the odour strength of the perfume to a convenient level. Alternatively, such lipophilic liquids may be added also or exclusively to provide other benefits to the perfume oil microemulsion. Thus, they may be added e.g. for their soothing, softening, healing, moisturizing or other beneficial action when applied to skin or hair. Also, the perfume oil may comprise other solid or liquid lipophilic components, such as colourants, preservatives, physiological coolants, viscosity modifiers, etc. Nevertheless, the perfume oil should comprise enough perfume to have the perfume oil microemulsion satisfy the intended perfuming qualities in its intended end use, e.g. provide a pleasant odour to the skin when applied thereto or to provide a pleasant odour to the environment (e.g. as air freshener) or to the microemulsion itself. Therefore, the content of actual perfume in the perfume oil should preferably be not less than 1% w/w (calculated on the total weight of perfume oil), more preferably at least 5%, most preferably at least 20%. Particularly useful microemulsions according to the invention contain perfume oil which comprises 50% w/w or more of perfume. Also, and independent from this, the content of actual perfume in the total microemulsion should not be less than 0.01% w/w of the microemulsion and preferably be more than 0.05% w/w, most preferably more than 0.1%. Also the actual perfume content in the microemulsion is preferably less than 25% by weight, more preferably less than 20%.

Likewise, the aqueous phase of the microemulsion may consist of water only, or it may comprise hydrophilic components having some beneficial property, either for the microemulsion itself or for its intended end use, such as viscosity modifiers, gelling agents, colourants, preservatives, anti-foam, humectants, etc.

For some applications it may be advantageous to also include a limited amount of lower aliphatic alcohol, particularly ethanol, either in the aqueous phase or the perfume oil or both. However, this should be less than 25%, preferably less than 10%, more preferably less than 5%, most preferably less than 1% w/w of the total microemulsion.

The surfactants to be used as primary surfactants are those having an HLB between 9 and 18. Mixtures of two or more different surfactants having a combined HLB between 9 and 18 are particularly useful. Preferably the HLB of such surfactants or surfactant mixtures is between 10 and 16. The quantity of surfactant is generally kept as low as possible since surfactants in most cases are only additives used to obtain the microemulsion, without having any additional beneficial effect on use of the microemulsion. The quantity necessary to obtain a clear and stable microemulsion obviously depends on the quantity of perfume oil. The maximum possible weight ratio of perfume oil to total surfactant in the microemulsion (perfume oil/surfactant ratio) tends increase with increasing perfume content in the microemulsion, which means that in general high perfume oil contents require proportionally less surfactant to obtain stable microemulsions than low perfume oil contents. Also, microemulsions containing 1% w/w or less lower aliphatic alcohols, may in some cases require perfume oil/surfactant ratios as low as 0.75. However, generally useful perfume oil/surfactant ratios in the microemulsion of the invention, and thus also in the mixtures of surfactant and perfume oil suitable therefore, will be in the range of 0.85–2.5, preferably the ratio is between 0.95 and 2.4, most preferably it is above 1.

Suitable non-ionic primary surfactants are e.g.:
ethoxylated alkylphenol ethers, particularly octyl- and nonylphenol ethers containing 5–20 EO;
ethoxylated aliphatic C6–C20 alcohols, which may be linear or branched and include Guerbet-type alcohols, containing 2–30 EO;
ethoxylated sterols containing 5–20 EO;
polyethylene glycol (2–10 EO) mono- and diesters of aliphatic C5–C11 carboxylic acids;
ethoxylated castor oil or hydrogenated caster oil derivatives containing 10–60 EO;

Preferred non-ionic surfactants have an HLB of between 10 and 16, have minimal odour and contain relatively short alkyl chains of 5–12 C-atoms, particularly of 5–10 C-atoms, such as:
ethoxylated alkylphenol ethers;
ethoxylated linear aliphatic C6–C10 alcohols;
ethoxylated branched aliphatic alcohols with a main aliphatic carbon chain of C6–C10;
ethoxylated mono- and di-esters of aliphatic C5–C7 carboxylic acids;
ethoxylated hydrogenated castor oils.

In addition to those mentioned above the following nonionic surfactants are very suitable:
mixed propoxylated/ethoxylated aliphatic C4–C16 aliphatic alcohols, particularly C8–C16;
ethoxylated hydrogenated castor oil monopyroglutamic monoisostearic diesters, ethoxylated glycerol monopyroglutamic monoisostearic diesters and other pyrrolidon carboxylic acid derivatives (such as Pyroter CPI-25 and Pyroter GPI-40 (Ajinomoto Co.))

Preferred ionic (anionic, cationic or amphoteric) primary surfactants contain relatively short alkyl chains of 6–12 C-atoms and comprise:
a) anionics: salts of sodium, potassium, ammonium or mono-, di- or triethanolamine, in particular:
alkarylsuphonates—e.g. sodium dodecylbenzenesulphonate, diethanolamine dodecylbenzene-sulphonate;
alcohol-sulphates—e.g. sodium lauryl-sulphate, ammonium lauryl-sulphate;
ether-sulphates—e.g. sodium laurylether-sulphate;
ether-phosphates—e.g. sodium laurylether-phosphate;
sulphosuccinates—e.g. sodium dioctylsulphosuccinate;
parrafin-sulphonates—e.g. sodium alkane-sulphonates;
sarcosinates—e.g. sodium lauryl-sarcosinate;
taurates—e.g. sodium N-methyl-N-cocoyl-taurate;
*isethionates—e.g. sodium cocoyl-isethionate;
protein-derived surfactants—e.g. sodium lauroylglutamate, triethanolamine coco hydrolysed collagen, sodium coco hydrolysed collagen.

b) cationics: in particular:
quaternary ammonium compounds—e.g. dioctyldimethylammonium chloride and lauryl-trimethylammonium chloride;
benzalkonium salts—e.g. benzalkonium chloride;
amine oxides—e.g. lauryl-dimethylamine oxide c) amphoterics, in particular betaines—e.g. betaine, cocoamidopropyl betaine The anionics indicated with * are especially preferred because of their mildness to the skin.

The actual choice of the primary surfactant(s) depends on the intended use of the microemulsion. If the microemulsion is to be used in another product, compatibility with the other components of that product is an important criterion determining this choice. Biodegradability may be another criterion. For microemulsions intended to be put on skin or hair the innocuousness of the surfactant(s) to skin or hair is one of the most important criteria. Many non-ionics and some anionics are particularly useful for that purpose.

The surfactant or surfactant mixture should be carefully selected so as to have an HLB which particularly suits the perfume oil. This may be done by testing the perfume oil in the desired concentration with a standard range of surfactant solutions with stepwise increasing HLB and selecting the HLB value giving the clearest microemulsion and/or the greatest range of temperature stability.

Additionally, the microemulsions, and the surfactant/perfume oil mixtures suitable therefore, comprise co-surfactants which significantly improve the solubilizing properties of the primary surfactants and/or provide extended temperature stability to the microemulsions. These co-surfactants may be of the ionic (cationic, anionic, amphoteric) or nonionic type, but the presence of at least a certain minimum quantity of ionic co-surfactant is required for optimum stability. Suitable ionic co-surfactants include the compounds mentioned above as primary surfactants and in addition e.g.: cetyl-trimethylammonium bromide and chloride, distearyl-dimethylammonium bromide and chloride, sodium stearate. Suitable nonionic co-surfactants comprise: aliphatic C6–C12 1,2-diols such as octan-1,2-diol, glucose ethers of aliphatic C6–C12 alcohols such as capryl glucoside, mono-, di- and triglycerides of C6–C12 aliphatic carboxylic acids such as glyceryl monooctanoate and trioctanoate, mono- and diesters of propylene glycol with C6–C12 aliphatic carboxylic acids, ethoxylated glyceryl esters of C6–C12 aliphatic carboxylic acids, higher aliphatic alcohols including Guerbet alcohols, propoxylated glucose methyl or ethyl ethers, propoxylated aliphatic C4–C16 alcohols, propoxylated and propoxylated/ethoxylated glyceryl ethers, alkylolamides such as lauric diethanolamide.

Co-surfactants are used in a quantity such as to comprise at most 50% w/w of the total surfactant, the remaining (at least 50%) being primary surfactant. By total surfactant is meant the total amount of primary surfactant(s) and co-surfactant(s). For non-ionic cosurfactants a more preferred percentage is 0–40%. Ionic co-surfactants should be present in a quantity of at least 0.5% w/w of the total surfactant. For ionic co-surfactants used in combination with non-ionic primary surfactants a more preferred percentage is 1–20% w/w. Those ionic surfactants, which may be used either as primary surfactants or as co-surfactants, are considered co-surfactants if their share in the total surfactant mixture is 20% or less. For many primary surfactant/co-surfactant combinations there is an optimum range of weight ratios which produces the best results. This range may be easily determined by testing a limited set of different ratios and determining which ratio gives the best solubilizing properties—i.e. allows the highest perfume oil: total surfactant ratio—or gives the greatest temperature stability. Co-surfactants are not limited to an HLB between 9 and 18; however, the influence of their HLB on the total HLB of the surfactant mixture should be taken into account.

As with the primary surfactants, the choice of the co-surfactant very much depends on the intended use of the microemulsion, and the same criteria determine this choice, e.g. compatibility with other components, biodegradability, skin compatibility etc., taking into account that the quantities of co-surfactant used are generally much less. For many purposes a very suitable surfactant mixture consist of non-ionic primary surfactants, if desired in combination with non-ionic co-surfactants, and 1–10% w/w, more preferably 1–5%, particularly 2–5% (of the total surfactant) ionic co-surfactant. Preferred ionic co-surfactants are anionics.

As already indicated, microemulsions have a limited temperature stability, i.e. they only remain clear within a limited temperature range. However, after having been taken out of this temperature range the microemulsions return to clarity after being brought back within the stable range. A greater temperature stability, i.e. an extended temperature range in which the microemulsion remains clear, may often be obtained by adding co-surfactants, as indicated above. Preferred microemulsions according to the invention will remain clear between 10° and 30° C.

As used herein the term "perfume" denotes a substantially water-insoluble composition of matter consisting of one or more perfume components, optionally mixed with a suitable solvent or diluent, which is used to impart a desired odour or flavour to the product to which it is added and/or to skin or hair. For the purpose of this invention the term "skin" is meant to include the oral cavity.

Perfume components are those constituents of a perfume which are added thereto only or primarily for their olfactive contribution. Perfume components and may be natural products such as essential oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Examples of such perfume components are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzylcarbinol, trichloromethylphenycarbinyl acetate, p-tert.butyl-cyclohexyl acetate, isononyl acetate, vetiveryl acetate, vetiverol, alpha-n-amylcinammic aldehyde, alpha-hexyl-cinammic aldehyde, 2-methyl-3-(p-tert.butylphenyl)-propanal, 2-methyl-3-(p-isopropylphenyl)propanal, 3-(ptert.butylphenyl)propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3-pentyltetrahydropyran, methyl dihydrojasmonate, 2-n-heptyl-cyclopentanone, 3-methyl-2-pentyl-cyclopentanone, n-decanal, n-dodecanal, 9-decenol-1, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methyl ionones, isomethyl ionones, irones, cis-3-hexenol and esters thereof, indane musks, tetralin musks, isochroman musks, macrocyclic ketones, macrolactone musks, ethylene brassylate, aromatic nitromusks.

Suitable solvents and diluents for perfumes as mentioned above are for example: diethyl phthalate, triethyl citrate, etc. Only limited quantities of alcoholic or other water-miscible solvents such as ethanol, isopropanol or dipropylene glycol will be present in the perfume i.e. 25% w/w of the perfume or less.

As already indicated, The HLB of the surfactant(s) is carefully selected to suit the particular perfume oil to be solubilized. Taking into account for any specific case the criteria for the choice of the surfactants, such as those mentioned above, this HLB can be obtained with different surfactants or surfactant mixtures. This HLB of surfactant mixtures may be calculated from the HLBs of the components, using the methods known in the art. Perfume oil: surfactant ratio and temperature stability may thereafter be optimized by adding cosurfactants, also as indicated above, taking into account that this addition will slightly modify the effective HLB of the total surfactant mixture.

The microemulsions of the invention may be prepared according to methods known in the art. A suitable method consists of adding the surfactant mixture to the perfume oil phase at such a temperature that a homogeneous mixture is obtained, thus producing the surfactant/perfume oil mixture which is also part of the present invention, followed by gradually adding the aqueous phase to this mixture while stirring until the w/o emulsion reverses to an o/w emulsion. Thereafter the remainder of the aqueous phase may be added more quickly. The temperature should not be higher than necessary to obtain a homogeneous surfactant/perfume oil mixture in order to prevent loss or deterioration of perfume.

The microemulsions according to the invention are suitable for a wide variety of applications and particularly for those applications where the use of organic solvents should be kept to a minimum. Examples are: aerosols for various purposes where a fire hazard may be involved, e.g. room deodorants and air fresheners; gel-type air fresheners; preparations for skin and hair, including in particular preparations for fine perfumery i.e. preparations primarily or exclusively intended for imparting an agreeable odour to the skin.

The following examples are illustrative of the clear microemulsions according to the invention. However, the invention is not limited thereto.

EXAMPLE 1

A light floral perfume, hereinafter referred to as "perfume 1", was prepared according to the following recipe:

|  | Percent/Weight |
| --- | --- |
| Amberoxide (10% in DEP*) | 0.5 |
| Amyl salicylate | 1.6 |
| Benzyl salicylate | 5.0 |
| Cassis Base 345F++ | 0.5 |
| Cedrenyl acetate | 7.0 |
| Cis-3-hexenyl acetate (10% in DPG**) | 1.4 |
| Cis-3-hexenyl salicylate | 1.4 |
| Cyclopentadecanolide | 3.2 |
| Diethyl phthalate | 30.0 |
| Galbanum Pure | 0.2 |
| Methyl dihydrojasmonate | 8.5 |
| Hexyl cinnamic aldehyde | 10.0 |
| Jacinthe Fleur 4914+++ | 1.6 |
| Jasmin 123 Type AB292A+ | 5.3 |
| LRG201 (50% in DEP*)+ | 1.5 |
| Mayciane 54++++ | 10.4 |
| Narcissus base 41370++ | 1.0 |
| Neroli AB 4869 (10% in DPG**)+ | 2.2 |
| Rosafolia AB462+ | 3.5 |
| Tuberose AB 1580+ | 1.0 |
| Undecanal (10% in DEP*) | 0.4 |
| Vetiveryl acetate | 2.8 |
| Ylang extra | 1.0 |
|  | 100.0 |

*Diethyl phthalate
**Dipropylene glycol
+Marketed by Quest International
++Marketed by Firmenich
+++Marketed by Synarome
++++Marketed by Lautier

EXAMPLE 2

A lavender fragrance suitable e.g. for air fresheners and hereinafter referred to as "perfume 2", was prepared according to the following recipe:

|  | Percent/Weight |
| --- | --- |
| α-pinene | 1.4 |
| β-pinene | 1.5 |
| Camphene | 0.4 |
| Cineole | 21.3 |
| Ocimene | 2.7 |
| Camphor | 7.7 |
| Dipropylene glycol | 19.2 |
| Linalol | 36.7 |
| Linalyl acetate | 7.4 |
| Limonene | 1.7 |
|  | 100.0 |

EXAMPLE 3

In the microemulsions according to the following recipes the perfume oil phase consists entirely of perfume 1. The microemulsions obtained were suitable as such as fine fragrance or as air fresheners.

|  | A | B | C | D |
| --- | --- | --- | --- | --- |
| Perfume 1 | 30.00 | 15.00 | 5.00 | 2.00 |
| Water | 52.85 | 73.25 | 90.45 | 96.18 |
| EO(9) nonyl phenyl ether | 9.60 | 6.05 | 2.35 | 0.94 |
| EO(12) nonyl phenyl ether | 6.15 | 4.90 | 1.90 | 0.76 |
| SLES** (30% aq) | 1.40 | 0.80 | 0.30 | 0.12 |

**Sodium lauryl ether sulphate

EXAMPLE 4

In the following examples the perfume oil phase of the microemulsions consists of perfume 1 and isopropyl myristate (a moisturiser). The microemulsions obtained are moisturizing fine fragrances.

|  | A | B |
| --- | --- | --- |
| Perfume 1 | 5.00 | 5.00 |
| Isopropyl myristate | 5.00 | 15.00 |
| Water | 81.00 | 62.75 |
| EO(6) nonyl phenyl ether | 2.00 | 6.75 |
| EO(9) nonyl phenyl ether | 6.50 | 9.50 |
| SLES (30% aq) | 0.50 | 1.00 |

EXAMPLE 5

In the microemulsions according to the following recipes the perfume oil phase consists entirely of the perfumes 1 and 2.

|  | A | B | C | D |
| --- | --- | --- | --- | --- |
| Perfume 1 | — | — | 5.00 | 5.00 |
| Perfume 2 | 5.00 | 5.00 | — | — |
| EO(5) C9/C11 alcohol* | 1.00 | 3.30 | — | — |
| EO(6) C9/C11 alcohol* | 0.20 | 0.20 | — | — |
| EO(7) C9/C11 alcohol* | 0.30 | 0.40 | — | — |
| EO(8) C9/C11 alcohol* | 1.00 | 0.60 | — | — |
| EO(11) C9/C11 alcohol* | 1.00 | 0.40 | — | — |
| EO(7) secondary alcohol** | — | — | 1.40 | 1.42 |
| EO(9) secondary alcohol** | — | — | 3.00 | 2.13 |
| EO(12) secondary alcohol** | — | — | 0.50 | 0.45 |
| 1,2 octanediol | 1.40 | — | — | — |
| PPG (26) buteth-26*** | — | — | — | 0.90 |
| Aerosol OT**** | 0.10 | 0.10 | 0.10 | 0.10 |
| Water | 90.00 | 90.00 | 90.00 | 90.00 |

*E.g. the Lutensol range marketed by BASF AG
**Nikkol BT range marketed by Nikko chemicals
***PO(26) EO(26) butyl ether
****Sodium dioctylsulphosuccinate marketed by Cyanamid B.V.

Microemulsions A and B are suitable as air fresheners or household cleaners; A illustrates the use of a non-ionic co-surfactant. C and D can be used as fine fragrances, air freshener of household cleaner. D has a much greater temperature stability than C even though it has the same total surfactant level.

EXAMPLE 6

Microemulsion A illustrates conventional solubilisation; B is the adjusted formulation according to the invention.

|  | A | B |
| --- | --- | --- |
| Perfume 2 | 0.50 | 0.50 |
| Cremophor RH40* | 1.75 | 0.25 |
| Dehydol O4** | — | 0.25 |
| Aerosol OT | — | 0.01 |
| Water | 97.75 | 98.99 |

*Ethoxylated hydrogenated castor oil marketed by BASF AG
**EO(4) octyl alcohol marketed by Henkel KGaA

EXAMPLE 7

Microemulsions A and B are examples of using higher levels of anionic and are suitable for household cleaners and/or air fresheners.

|  | A | B |
|---|---|---|
| Perfume 2 | 5.00 | 5.00 |
| EO(6) nonyl phenyl ether | 1.30 | 1.25 |
| EO(9) nonyl phenyl ether | 2.20 | 2.00 |
| Ucon 50-HB-660* | — | 0.50 |
| SDBS** | 1.50 | 1.25 |
| Water | 90.00 | 90.00 |

*PO(12) EO(16) butyl ether
**Sodium dodecylbenzene-sulphonate

EXAMPLE 8

Mentioned below are examples of surfactant/perfume mixtures suitable for preparing perfume microemulsions and taken from the examples above. In some cases it may be necessary to slightly increase the proportion of surfactant to perfume to solubilise low levels of perfume (e.g. $\leq 0.5\%$) in water. These mixtures are suitable for the examples of microemulsions given above.

|  | A | B | C | D |
|---|---|---|---|---|
| Perfume 1 | 52.4 | — | — | 50.0 |
| Perfume 2 | — | 49.5 | 50.0 | — |
| EO(6) nonyl phenyl ether | — | — | 12.5 | — |
| EO(9) nonyl phenyl ether | 24.6 | — | 20.0 | — |
| EO(12) nonyl phenyl ether | 19.9 | — | — | — |
| SDBS | — | — | 12.5 | — |
| Aerosol OT | — | 1.0 | — | 1.0 |
| Ucon 50-HB-660 | — | — | 5.0 | — |
| Cremophor RH40 | — | 24.75 | — | — |
| Dehydol 04 | — | 24.75 | — | — |
| EO(7) secondary alcohol | — | — | — | 14.2 |
| EO(9) secondary alcohol | — | — | — | 21.3 |
| EO(12) secondary alcohol | — | — | — | 4.5 |
| PPG(26) buteth-26 | — | — | — | 9.0 |
| SLES (30% aq) | 3.1 | — | — | — |

We claim:
1. A clear o/w microemulsion comprising 0.01–40% w/w of perfume oil, at least 40% w/w of an aqueous phase, less than 10% w/w of lower aliphatic alcohol and a surfactant mixture comprising at least 50% of one or more primary surfactants with HLB between 9 and 18 and 0.5–50% of one or more co-surfactants, at least one co-surfactant being an ionic co-surfactant, wherein the weight ratio of perfume oil to surfactant mixture is between 0.85 and 2.5, wherein the primary surfactants are chosen from:
  i. the non-ionic primary surfactants below:
    ethoxylated alkylphenol ethers containing 5–20 EO;
    ethoxylated linear aliphatic C6–C10 alcohols containing 2–30 EO;
    ethoxylated branched aliphatic alcohols with a main aliphatic carbon chain of C6–C10 and containing 2–30 EO;
    ethoxylated sterols containing 5–20 EO;
    polyethylene glycol (2–10 EO) mono- and diesters of aliphatic C5–C11 carboxylic acids;
    ethoxylated castor oil or hydrogenated castor oil derivatives containing 10–60 EO;
    mixed propoxylated/ethoxylated aliphatic C4–C16 aliphatic alcohols, particularly C8–C16;
    ethoxylated hydrogenated castor oil monopyroglutamic monoisostearic diesters, ethoxylated glycerol monopyroglutamic monoisostearic diesters and other pyrrolidon carboxylic acid derivatives;
  ii. the ionic primary surfactants containing alkyl chains of 6-12 C-atoms below:
    (a) anionics: sodium, potassium, ammonium or mono-, di- or triethanolamine salts of alkaryl-suphonates, alcohol-sulphates, ether-sulphates, etherphosphates sulphosuccinates, paraffin-sulphonates, sarcosinates, taurates, isethionates, protein-derived surfactants;
    (b) cationics: quaternary ammonium compounds, benzalkonium salts, amine oxides;
    (c) amphoterics,
and wherein the co-surfactants are chosen from:
  i. the ionic primary surfactants mentioned above and: cetyl-trimethylammonium bromide and chloride, distearyl-dimethylammonium bromide and chloride, sodium stearate;
  ii. non-ionics surfactants mentioned below: aliphatic C6–C12 1,2-diols, glucose ethers of aliphatic C6–C12 alcohols, mono-, di- and triglycerides of C6–C12 aliphatic carboxylic acids, mono- and diesters of propylene glycol with C6–C12 aliphatic carboxylic acids, ethoxylated glyceryl esters of C6–C12 aliphatic carboxylic acids, higher aliphatic alcohols including Guerbet alcohols, propoxylated glucose methyl or ethyl ethers, propoxylated aliphatic C4–C16 alcohols, propoxylated and propoxylated/ethoxylated glyceryl ethers, alkylolamides.

2. Microemulsion according to claim 1 which comprises less than 5% w/w, of lower aliphatic alcohol.

3. A clear o/w microemulsion comprising 0.01–40% w/w of perfume oil, at least 40% w/w of an aqueous phase, less than 1% w/w of lower aliphatic alcohol and a surfactant mixture comprising at least 50% of one or more primary surfactants with HLB between 9 and 18 and 0.5–50% of one or more co-surfactants, at least one co-surfactant being an ionic co-surfactant, wherein the weight ratio of perfume oil to surfactant mixture is between 0.75 and 2.5, wherein the primary surfactants are chosen from:
  i. the non-ionic primary surfactants below:
    ethoxylated alkylphenol ethers containing 5–20 EO;
    ethoxylated linear aliphatic C6–C10 alcohols containing 2–30 EO;
    ethoxylated branched aliphatic alcohols with a main aliphatic carbon chain of C6–C10 and containing 2–30 EO;
    ethoxylated sterols containing 5–20 EO;
    polyethylene glycol (2–10 EO) mono- and diesters of aliphatic C5–C11 carboxylic acids;
    ethoxylated castor oil or hydrogenated castor oil derivatives containing 10–60 EO;
    mixed propoxylated/ethoxylated aliphatic C4–C16 aliphatic alcohols, particularly C8–C16;
    ethoxylated hydrogenated castor oil monopyroglutamic monoisostearic diesters, ethoxylated glycerol monopyroglutamic monoisostearic diesters and other pyrrolidon carboxylic acid derivatives;
  ii. the ionic primary surfactants containing alkyl chains of 6-12 C-atoms below:
    (a) anionics: sodium, potassium, ammonium or mono-, di- or triethanolamine salts of alkaryl-suphonates, alcohol-sulphates, ether-sulphates, etherphosphates sulphosuccinates, paraffin-sulphonates, sarcosinates, taurates, isethionates, protein-derived surfactants;

(b) cationics: quaternary ammonium compounds, benzalkonium salts, amine oxides;
(c) amphoterics,
and wherein the co-surfactants are chosen from:
i. the ionic primary surfactants mentioned above and: cetyl-trimethylammonium bromide and chloride, distearyl-dimethylammonium bromide and chloride, sodium stearate;
ii. non-ionics surfactants mentioned below: aliphatic C6–C12 1,2-diols, glucose ethers of aliphatic C6–C12 alcohols, mono-, di- and triglycerides of C6–C12 aliphatic carboxylic acids, mono- and diesters of propylene glycol with C6–C12 aliphatic carboxylic acids, ethoxylated glyceryl esters of C6–C12 aliphatic carboxylic acids, higher aliphatic alcohols including Guerbet alcohols, propoxylated glucose methyl or ethyl ethers, propoxylated aliphatic C4–C16 alcohols, propoxylated and propoxylated/ethoxylated glyceryl ethers, alkylolamides.

4. Microemulsion according to claim 1 or 3 comprising ionic co-surfactant in an amount of 1–20% w/w and optionally non-ionic co-surfactant in an amount of 0–40% of the surfactant mixture.

5. Microemulsion according to claim 1 or 3 wherein the primary surfactants have an HLB of between 10 and 16, have minimal odor and are chosen from:
i. those having alkyl chains of between 5 and 12 C-atoms and below to the groups:
ethoxylated alkylphenol ethers;
ethoxylated linear aliphatic C6–C10 alcohols;
ethoxylated branched aliphatic alcohols with a main aliphatic carbon chain of C6–C10;
ethoxylated mono- and diesters of aliphatic C5–C7 carboxylic acids;
ethoxylated hydrogenated castor oil;
ii. those belonging to the groups:
mixed propoxylated/ethoxylated aliphatic C8–C16 aliphatic alcohols;
ethoxylated hydrogenated castor oil monopyroglutamic monoisostearic diesters, ethoxylated glycerol monopyroglutamic monoisostearic diesters and other pyrrolidon carboxylic acid derivatives.

6. Microemulsion according to claim 1 or 3 wherein the weight ratio of perfume oil to surfactant mixture is above 1.

7. Microemulsion according to claim 1 or 3 wherein the perfume oil comprises at least 1% of its weight of perfume.

8. Microemulsion according to claim 1 or 3 wherein the surfactant mixture consists of non-ionic primary surfactants in combination with 0–40% non-ionic co-surfactants and 1–10% w/w (of the surfactant mixture) ionic co-surfactants.

9. Microemulsion according to claim 8 wherein the ionic co-surfactant is anionic.

10. Microemulsion according to claim 1 or 3 wherein the actual perfume content is less than 25% by weight of the total emulsion.

11. A process for perfuming skin or hair which comprises applying to the skin or hair a microemulsion according to claim 1 or claim 3.

12. A process according to claim 11 wherein the microemulsion comprises at least 3% w/w of perfume oil.

13. A process according to claim 11 wherein the perfume oil comprises at least 20% of its weight of perfume.

14. A process according to claim 11 wherein the primary surfactant is non-ionic.

15. A surfactant/perfume oil mixture suitable for preparing a clear o/w microemulsion according to claim 1 wherein the weight ratio of perfume oil to total surfactant is between 0.85 and 2.5.

16. Surfactant/perfume oil mixture according to claim wherein the ratio is above 1.

* * * * *